United States Patent
Saranathan et al.

(10) Patent No.: US 9,454,709 B2
(45) Date of Patent: Sep. 27, 2016

(54) METHOD FOR RAPID-MULTICONTRAST BRAIN IMAGING

(71) Applicant: The Board of Trustees of the Leland Stanford Junior University, Palo Alto, CA (US)

(72) Inventors: Manojkumar Saranathan, Redwood City, CA (US); Brian K. Rutt, Stanford, CA (US); James A. Rioux, San Jose, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/539,061

(22) Filed: Nov. 12, 2014

(65) Prior Publication Data

US 2016/0132746 A1   May 12, 2016

(51) Int. Cl.
| | |
|---|---|
| G06K 9/00 | (2006.01) |
| G06K 9/46 | (2006.01) |
| G06T 7/00 | (2006.01) |
| A61B 5/00 | (2006.01) |
| A61B 5/055 | (2006.01) |
| G01R 33/48 | (2006.01) |
| G01R 33/56 | (2006.01) |

(52) U.S. Cl.
CPC ........... *G06K 9/4633* (2013.01); *A61B 5/0042* (2013.01); *A61B 5/055* (2013.01); *A61B 5/742* (2013.01); *G01R 33/482* (2013.01); *G01R 33/5601* (2013.01); *G06K 9/4647* (2013.01); *G06K 9/4652* (2013.01); *G06T 7/0012* (2013.01); *G06T 7/0061* (2013.01); *G06T 7/0065* (2013.01); *G06T 7/0087* (2013.01); *A61B 2576/026* (2013.01); *G06K 2009/4657* (2013.01); *G06K 2209/051* (2013.01); *G06T 2207/10096* (2013.01); *G06T 2207/20076* (2013.01); *G06T 2207/30016* (2013.01); *G06T 2207/30196* (2013.01)

(58) Field of Classification Search
None
See application file for complete search history.

(56) References Cited

U.S. PATENT DOCUMENTS

| | | | |
|---|---|---|---|
| 6,748,098 B1* | 6/2004 | Rosenfeld | G06T 3/4007 382/131 |
| 8,638,096 B2 | 1/2014 | Zhang et al. | |
| 2003/0011368 A1* | 1/2003 | Abe | G01R 33/563 324/309 |
| 2008/0197842 A1* | 8/2008 | Lustig | G01R 33/561 324/307 |
| 2010/0205143 A1* | 8/2010 | Kroeker | G01R 33/4818 707/602 |
| 2011/0006768 A1* | 1/2011 | Ying | G01R 33/5611 324/309 |
| 2012/0092009 A1* | 4/2012 | Zhang | G01R 33/5611 324/309 |
| 2013/0123611 A1* | 5/2013 | Riederer | G01R 33/4818 600/419 |
| 2014/0125335 A1* | 5/2014 | Li | G01R 33/4822 324/309 |
| 2014/0266193 A1 | 9/2014 | Kecskemeti et al. | |

* cited by examiner

*Primary Examiner* — Shervin Nakhjavan

(74) *Attorney, Agent, or Firm* — Beyer Law Group LLP

(57) ABSTRACT

A method for providing an image of a subject is provided. The plurality of Cartesian points is divided into a first group and a second group, wherein all of the Cartesian points in the first group have a $k_r$ that is less than or equal to $k_r$ of all of the Cartesian points in the second group. The second group is divided into N subgroups. An inversion recovery radio frequency is applied to the subject. K-space data for the first group of Cartesian points for M different time periods is acquired, wherein k-space data is acquired for only one sub-group sequentially and cyclically for the M different time periods. For each time period i of the M different time periods, acquired k-space data for the first group of Cartesian points at time period i and k-space data from N consecutive subgroups of Cartesian points.

18 Claims, 7 Drawing Sheets

METHOD FOR RAPID-MULTICONTRAST BRAIN IMAGING

GOVERNMENT RIGHTS

This invention was made with Government support under contract EB015891 and RR026351-01A1 awarded by the National Institutes of Health. The Government has certain rights in this invention.

BACKGROUND OF THE INVENTION

This invention relates generally to magnetic resonance imaging (MRI). More specifically, the invention relates to multi-contrast MRI.

SUMMARY OF THE INVENTION

In accordance with the invention, a method for providing an image of a subject in a magnetic resonance imaging MRI system is provided. A plurality of Cartesian points is defined on a $k_y$-$k_z$ plane with a center, wherein each of the plurality of Cartesian points has a $k_r$, wherein $k_r$ is a distance from a Cartesian point of the plurality of Cartesian points to the center. The plurality of Cartesian points is divided into a first group (Group A) and a second group (Group B), wherein all of the Cartesian points in the first group have a $k_r$ that is less than or equal to $k_r$ of all of the Cartesian points in the second group. The second group is divided into N subgroups, wherein N is a whole number greater than or equal to two, wherein the subgroups have an incoherent point spread function. A radio frequency inversion pulse is applied to the subject such that a net longitudinal magnetization in the subject is substantially inverted and begins to relax back to equilibrium. K-space data for the first group of Cartesian points for M different time periods is acquired, wherein k-space data is acquired for only one sub-group for each time period of the M different time periods, and wherein k-space data is acquired for each subgroup sequentially and cyclically for the M different time periods. For each time period i of the M different time periods, acquired k-space data for the first group of Cartesian points at time period i and k-space data from N consecutive subgroups of Cartesian points where one of the N consecutive subgroups is the subgroup that is acquired during time period i is used to create image data of the subject for first time period i.

The invention and objects and features thereof will be more readily apparent from the following detailed description and appended claims when taken with the drawings.

BRIEF DESCRIPTION OF THE DRAWINGS

FIG. 2a shows the k-space weighting TI ms after the inversion pulse and the proposed radial acquisition scheme.

FIG. 2b shows a point spread function (PSF) that arises from the k-space weighting shown in FIG. 2a.

FIGS. 2c-d illustrate when k-space weighting when the Bi points are acquired sequentially and the corresponding PSF.

DETAILED DESCRIPTION OF ILLUSTRATED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Figure 1:
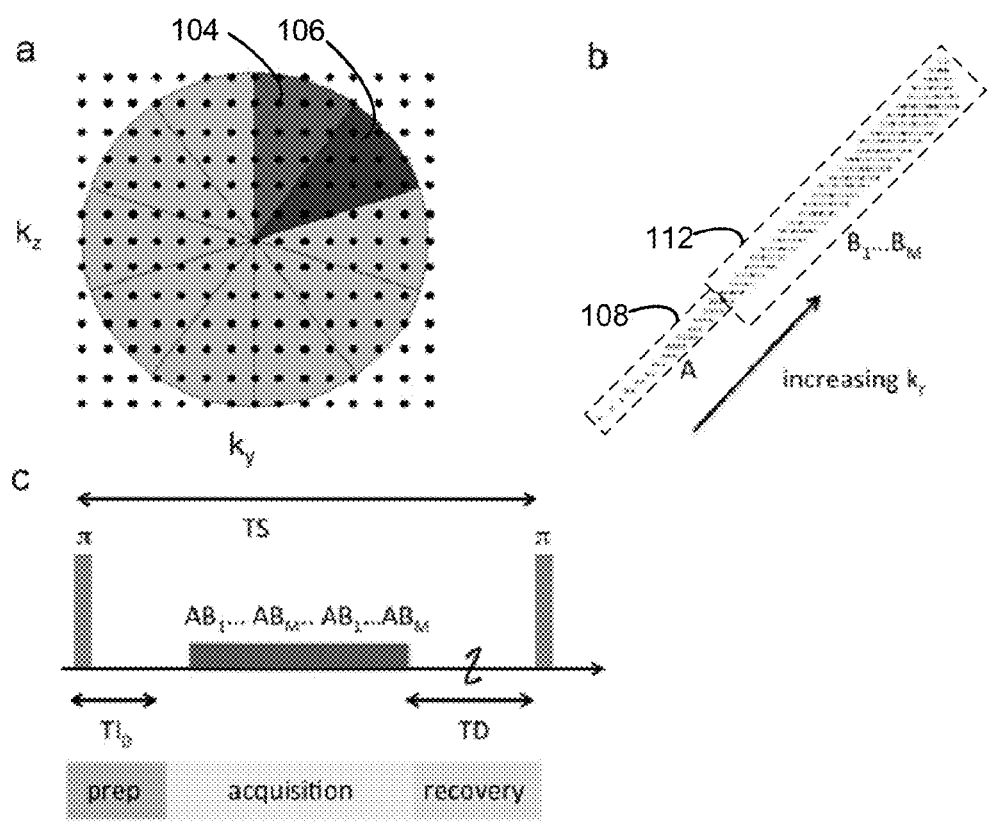
FIG. 1a shows the sampling scheme in $k_y$-$k_z$ space divided into radial sectors.
FIG. 1b shows groupings of Cartesian points.
FIG. 1c shows the pulse sequence and acquisition order

Inversion recovery (IR) imaging is typically performed as part of an MR imaging protocol to enhance image contrast by nulling the desired tissue of interest using an inversion pulse and an inversion recovery delay period (TI) followed by data acquisition. In neuroimaging, cerebral spinal fluid (CSF) is commonly nulled to produce images where the CSF is dark. Other tissue types such as white matter (WM) or grey matter (GM) can also be nulled to highlight lesions in brain pathology such as multiple sclerosis or visualize the thalamic nuclei. A typical 3D brain scan with 1 mm³ isotropic spatial resolution and whole-brain coverage is acquired in a scan time of 5 to 10 min, depending on the desired contrast and image signal-to-noise ratio (SNR). Only one tissue can be nulled at a time, requiring multiple repetitions of this scan with different inversion delay TI, if multiple types of contrast or a $T_1$ map are desired. This increases overall exam time, making the process motion sensitive and requiring post-processing correction, if the multiple TI data are to be fitted to generate a $T_1$ map. An embodiment provides a technique that can yield a series of 3D volumes spanning a range of desired inversion times (i.e. contrasts), all acquired in a single scan. The scan time is comparable to that of conventional IR imaging (5-10 min). This embodiment also utilizes existing commercially available (vendor supplied) reconstruction software, without the need for offline reconstruction.

k-space sampling: FIG. 1a shows the sampling scheme in $k_y$-$k_z$ space divided into radial sectors for an embodiment of the invention. For the sake of simplicity, parallel imaging is not shown in this example although the actual scanner implementation used the view sharing concepts described here along with undersampling in two dimensions ($k_y$ and $k_z$) with parallel imaging (ARC) reconstruction. The corners of elliptical k-space are skipped resulting in ~22% reduction in scan time. The remaining points inside the elliptical region are divided into radial sectors by sorting the points angularly, with the number of points per sector N dependent on the desired "temporal resolution" i.e. the spacing of the desired TIs. The main innovation that allows rapid generation of multiple TI contrast images is the use of view sharing within each radial sector with minimal artifacts by judicious choice of sampling patterns. One acquisition strategy is as follows:

i) within each radial sector, sort the points in the order of increasing $k_r$ (the radial distance from the origin).

ii) designate the first $N_A$ points as region A 108 forming a first group. The remaining (N-$N_A$) points in each sector are divided into M regions we call $B_i$ (i=1 ... M) forming a second group with M subgroups. This is shown in FIG. 1b with A regions represented by dots in the first region 108 and the B regions 112 (3 in this case) by differently shaded dots.

iii) The $B_i$ regions are spread out as much as possible both within the sector as well as relative to neighboring sectors (see next section for rationale) in order make the PSF incoherent. In order to accomplish this, the following dithering scheme is used that alters the interleaving pattern from sector to sector. Start with a number j from 1 to M. The first $B_i$ region is created by indexing j, j+M, j+2*M ... into the array of Bi points. The next $B_i$ region is created by indexing j+1, j+1+M, j+1+2*M into the Bi points array and so on until all M $B_i$ regions are created. For the neighboring sectors, a different j is used as the starting index. One simple way to achieve this is to make j a function of the sector number and cycle it. Another way is to randomly permute [1 ... M] and use that as a starting j. This dithering ensures that if sector k region $B_i$ starts with a point in the first group, then sector k+1, region $B_i$ is in the second group and so on, resulting in an incoherent randomized pattern.

Figure 2:
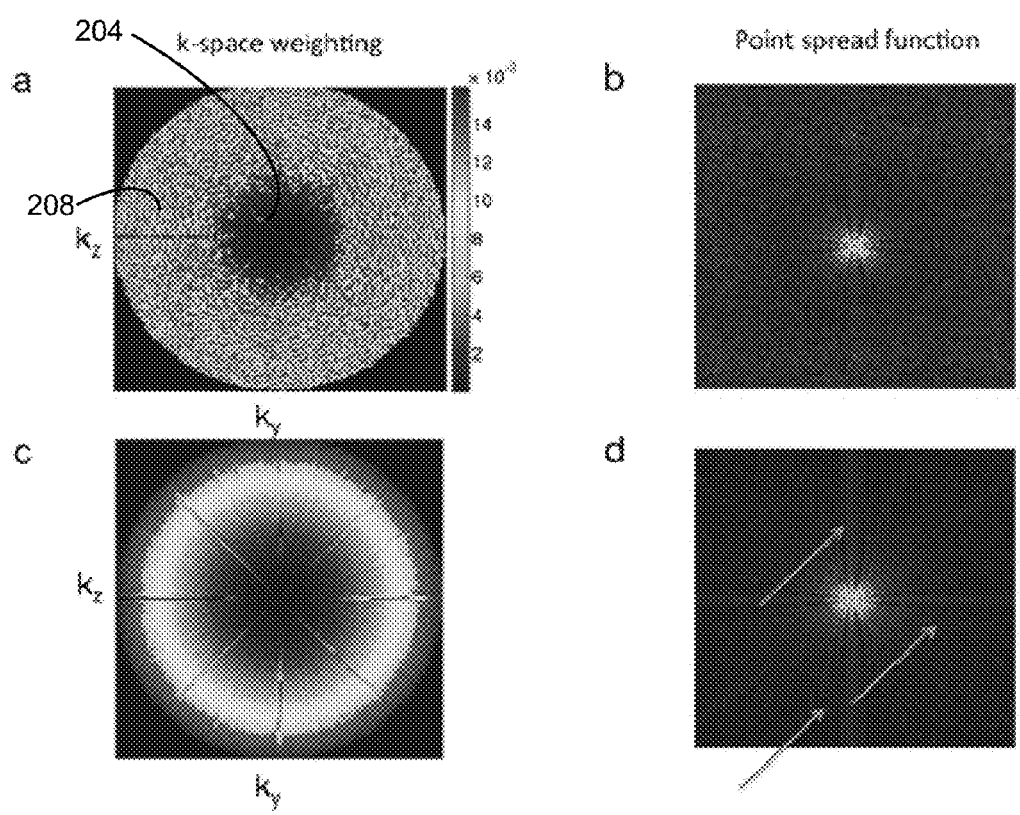

Data acquisition: After each inversion pulse, this embodiment acquires k-space points in the following schedule: $AB_1AB_2...AB_M$ (FIG. 1c, which shows the pulse sequence and acquisition order). This pattern can be repeated multiple times or cycles during the recovery period, if needed, to cover the desired range of TI. Following a recovery period TD, the entire process is repeated for the next radial sector and so on until all radial sectors (i.e. all k-space) are covered. In FIG. 1a, regions 104, 106 represent two successive radial sectors. Since data is acquired during the inversion recovery process, there is a k-space weighting that is introduced. Ideally, this should be flat or, at the very least, smooth, to minimize any artifacts from the modulation of k-space. The k-space weighting for the proposed scheme for the phase where WM is nulled is shown in FIG. 2a for the WM signal. The "central" region 204 represents the signal in the A regions and the multishaded outer annulus 208 represents that of the $B_i$ regions. The 2D Fourier transform of this 2D modulation function is essentially the point spread function (PSF), which is shown in FIG. 2b, a good measure of the degree of ghosting/blurring to be expected from the different sampling and weighting schemes. Note that the interleaving scheme helps disperse the weighting function over the outer k-space regions (i.e. region outside the central disk) resulting in incoherent PSF compared to a scheme where the Bi points are acquired sequentially. The sequential scheme and the correspondent PSF is shown in FIGS. 2c and 2d respectively.

Image reconstruction: In order to form a complete AB region for each $AB_i$ region acquired, missing k-space data from the neighboring $B_j$ (j not equal to i) are copied in acquisition memory to form a full AB region i.e. the $B_i$ regions are all shared for each A region and this speeds up the acquisition. Note that a full 3D volume is created for every $AB_i$ region, resulting in a speedup of (N-1) to N-fold depending on the parameters chosen. The contrast for each volume is determined by the temporal distance between the inversion pulse and the time when the A region is acquired. The copying is done during the TD recovery period resulting in no additional reconstruction latency.

Alternative sampling scheme 1: The interleaving of the $B_i$ regions disperses them making the PSF incoherent. This is useful for reducing artifacts that arise when k-space data from different parts of a signal recovery curve are combined together. This could also be useful for reconstruction of just the partial $AB_i$ data using compressive sensing instead of view sharing with the neighboring $AB_i$ data. FIG. 2a-b shows one possible scheme of into subdividing radial sectors into Bi regions. An interleaved spiral sampling scheme can also accomplish the same goal:

i) Start with the elliptical region as in the previous case and instead of dividing it into radial sectors, we create spiral interleaves (with the same N points per interleave). The acquisition and reconstruction scheme are identical to the radial sector case.

ii) The spiral interleaves are created as follows:
a) Sort all the points in the order of increasing $k_r + k_\theta/2\pi$ (the angle part given by $\arctan(k_z/k_y)$ is added to ensure smoothness of traversal).
b) The total k-space points in the ellipse $N_{tot}$ is divided into $[N_{tot}/N]=M$ interleaves.
c) Each interleaf is created as follows-start with a random number j from 1 to m. The first interleaf is created by indexing j, j+m, j+2*m ... into the $k_y$-$k_z$ points array. The next interleaf is indexed as k, k+m, k+2*m, where k is another random number from 1 to M with j excluded and so on. One simple way to achieve this is to store a random permutation of the integer list [1 ... m] in an array rsort and start each interleaf j with rsort[j] to create m interleaves.
d) Each interleaf is subdivided into A and $B_i$, just like in the radial sector sampling scheme (the first $N_A$ points are designated as A and the remaining points interleaved by a factor of M into M $B_i$ regions) with the same dithering mechanism.

Figure 3:
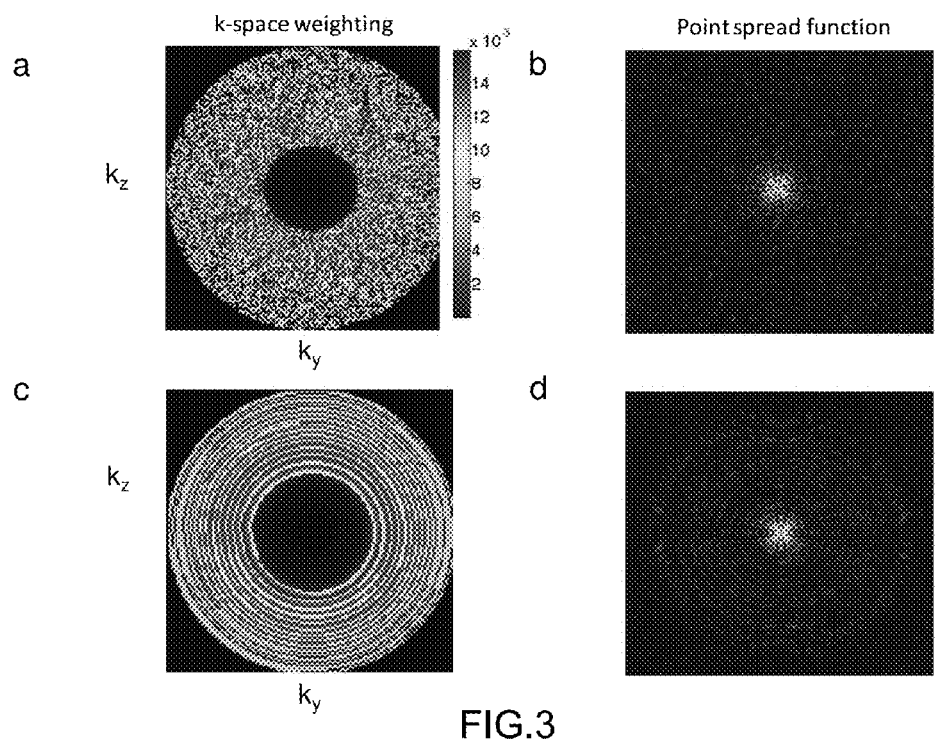
FIGS. 3a-b shows the k-space weighting TI ms after the inversion pulse and the proposed spiral acquisition scheme (4 interleaves) and the corresponding PSF.
FIGS. 3c-d show the same spiral scheme, as shown in FIGS. 3a-b but without dithering the points resulting in a coherent PSF (d).

The use of randomized starting points (dithering) in the interleaving is crucial in eliminating any coherence that would result from sequential starting points. FIG. 3a-b shows an example with only 4 interleaves shown for clarity. As before, the first $N_A$ points in each interleaf is red and the remaining black, cyan and magenta. The k-space weighting is shown in 3b and it can be seen that the pattern and as well as PSF (3b) is incoherent. FIG. 3c shows the k-space weighting for a spiral interleaving scheme where the starting points are not randomized and the corresponding PSF (3d), clearly demonstrating the ability of the randomization scheme in making the weighting and PSF incoherent.

Alternative sampling scheme 2: Instead of following a deterministic algorithm (like radial or spiral interleaving) to subdivide the B region into subregions, one can simply use a random or, more practically, a pseudo-random subset of points in B and create M such dispersed Bi regions. In order to avoid "clumping" or large "holes" i.e. keep the mean distance between points more or less uniform, a Poisson Disk scheme similar to what is used in compressed sensing, which is described in U.S. Pat. No. 8,638,096 by Zhang et al., entitled "Method of autocalibrating parallel imaging interpolation from arbitrary K-space sampling with noise correlations weighted to reduce noise of reconstructed images" and issued Jan. 28, 2014 and which is incorporated by reference for all purposes, can be used, which enforces a maximum distance criterion for the distance between the points. The central region can be chosen as a suitable fraction of the whole set of points ($N_A$) with $N_A+N_B=N_{tot}$ the total number of ky-kz points Results/Proof of Concept:

The radial fanbeam based scheme (FIG. 1a-b) was implemented on both GE 3T (750) and 7T (950) MRI systems and healthy human subjects were scanned after informed consent. A 1 mm isotropic acquisition covering the whole brain was acquired. This embodiment used the following parameters: 16-18 cm FOV, 160×160×160 matrix, 1 mm thick slices, N=47 points per radial sector, Na=11, m=3 (i.e. 3 B regions with 12 points each). The size of the ABi portion of each radial sector was 23, which is about 110 ms for TR=5 ms. The pattern was repeated twice to produce 6 phases. The delay after the inversion pulse $TI_0$ was chosen to be 400-500 ms so that the first or second phase was WM-nulled and the last phase CSF nulled. TS was set to 2s. The total scan time was about 7.5 min. A custom MATLAB script was used to simulate the MPRAGE signal equations for different species of interest and this was used to select $TI_0$ as well as the flip angle for optimal signal-to-noise ratio.

Figure 4:
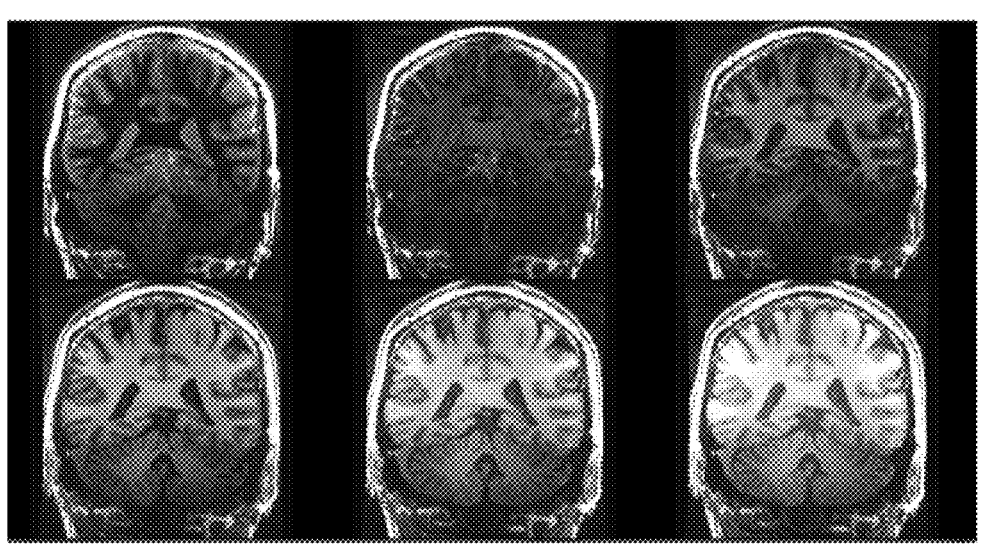
FIG. 4 shows a representative slice from each of the 6 phases acquired from a healthy volunteer on a 7T scanner.
Figure 5:
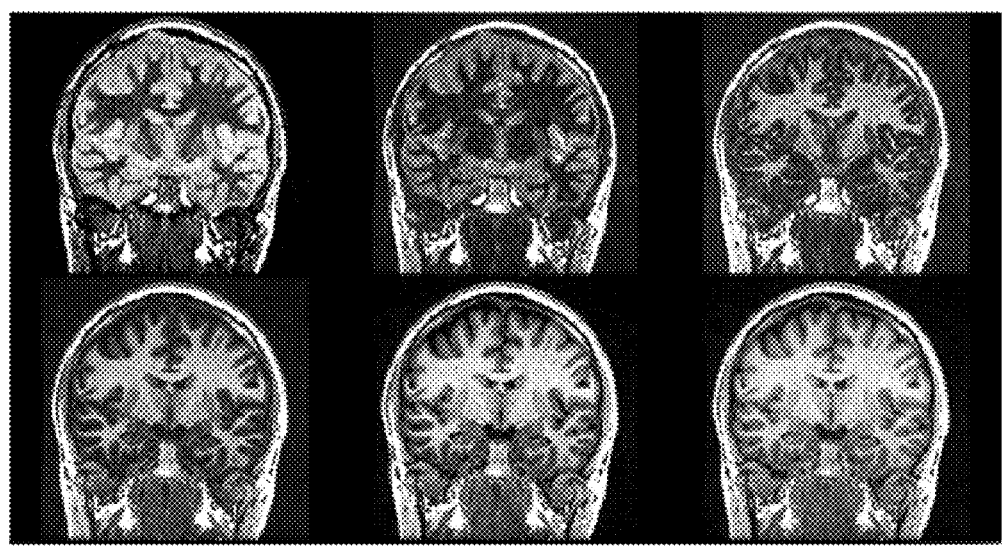
FIG. 5 shows similar data obtained from a healthy subject on a 3T scanner.

FIG. 4 shows a representative slice from each of the 6 phases acquired from a healthy volunteer on a 7T scanner. The first phase shows nulled WM, the second with the WM-GM transition zone nulled, the third with GM-nulled, the fourth phase with GM-CSF interface nulled and the last two phases with nulled CSF. FIG. 5 shows similar data obtained from a healthy subject on a 3T scanner. The 3T data was acquired using an 8-channel coil whilst the 7T data using a 32 channel receive array (Nova) accounting for the slightly noisier 3T data. Note the high spatial resolution and minimal artifacts in both cases.

Some of the advantages provided by some of the embodiments are the ability to generate multiple TI contrast images in short scan times (essentially the time required for a conventional single contrast (IR) 3D scan which is on all standard brain imaging protocols), allowing view ordering schemes that are tailored to minimize artifacts when combining using view sharing or reconstruction using compressive sensing, and incorporation of view copying during the recovery period to minimize any reconstruction errors and obviating the need for a new reconstruction engine, which makes the dissemination of the application facile.

Applications

The most straightforward application is the generation of registered 3D images with multiple TI (i.e. different contrast weighting) in short scan times of <10 minutes. The availability of multiple contrast volumes can be used to improve brain segmentation as well as to better delineate the thalamic nuclei, which have differing $T_1$ resulting in different nuclei "enhancing" on different phases. The data can also be used to generate a 3D $T_1$ map. While we have used brain imaging as an application to demonstrate the power of this technique, it can be used in other applications like fast T1 mapping in the body.

OTHER EMBODIMENTS

While we have demonstrated clinical results from the proposed view sharing technique, we have also developed trajectories with incoherent PSFs that are suitable for reconstruction using compressed sensing. PSF incoherence is a critical factor in the performance of CS reconstruction algorithms. In practice, a combination of VS and CS could yield the best results. For example, if B is divided into 4 regions, then $AB_1+B_2$ could be reconstructed using CS. The use of both $B_1$ and $B_2$ helps reduce the size of the gaps compared to just $B_1$ or $B_2$, making the CS reconstruction more robust. This still reduces the temporal footprint by a factor of 2 compared to VS, which would require $B_3$ and $B_4$ as well to generate a full k-space. Smaller temporal footprint will reduce the artifacts from changing signal across the curve, which could be used to increase flip angle or lower bandwidth for improving SNR.

Both the schemes can be made motion robust by employing a golden angle type reordering of the angular sectors or spiral interleaves. This would further disperse any coherence in the k-space weighting function.

The multi TI data can also be fitted using a Look-Locker inversion recovery equation to generate whole brain $T_1$ maps. This fit yields an effective $T_1$ relaxation time that depends on the sequence repetition time TR and the flip angle, and with knowledge of these parameters, can be converted into an estimate of the true tissue $T_1$. It is also possible to perform a ratio-based $T_1$ estimation that is more robust to $B_1$ heterogeneity (which is a big issue at ultra high field strengths) from 2 or 3 different TI data, similar to MP2RAGE and MP3RAGE methods.

Figure 6:
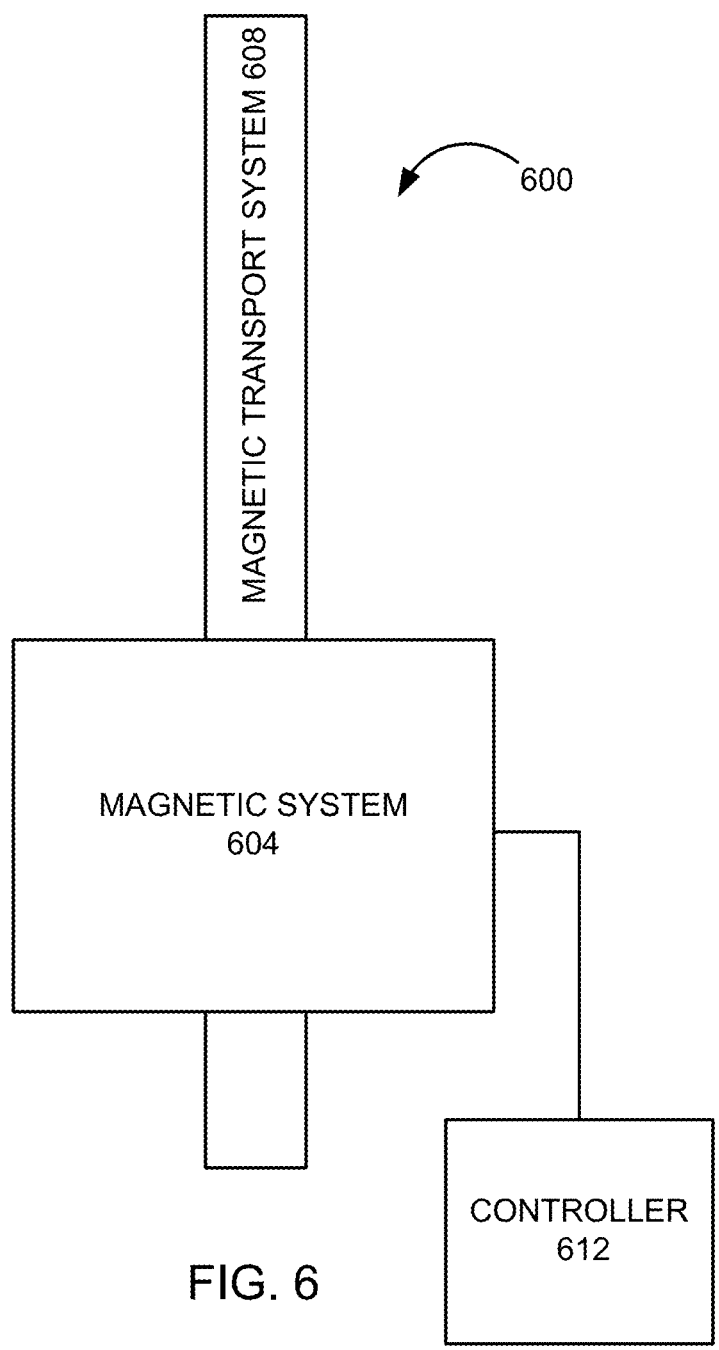
FIG. 6 is a schematic top view of a magnetic resonance imaging (MRI) system 600 that may be used in an embodiment of the invention.

To further facilitate understanding of the invention, FIG. 6 is a schematic top view of a magnetic resonance imaging (MRI) system 600 that may be used in an embodiment of the invention. The MRI system 600 comprises a magnet system 604, a patient transport table 608 connected to the magnet system, and a controller 612 controllably connected to the magnet system. In one example, a patient (subject) would lie on the patient transport table 608 and the magnet system 604 would pass around the patient. The controller 612 would control magnetic fields and radio frequency (RF) signals provided by the magnet system 604 and would receive signals from detectors in the magnet system 604.

Figure 7:
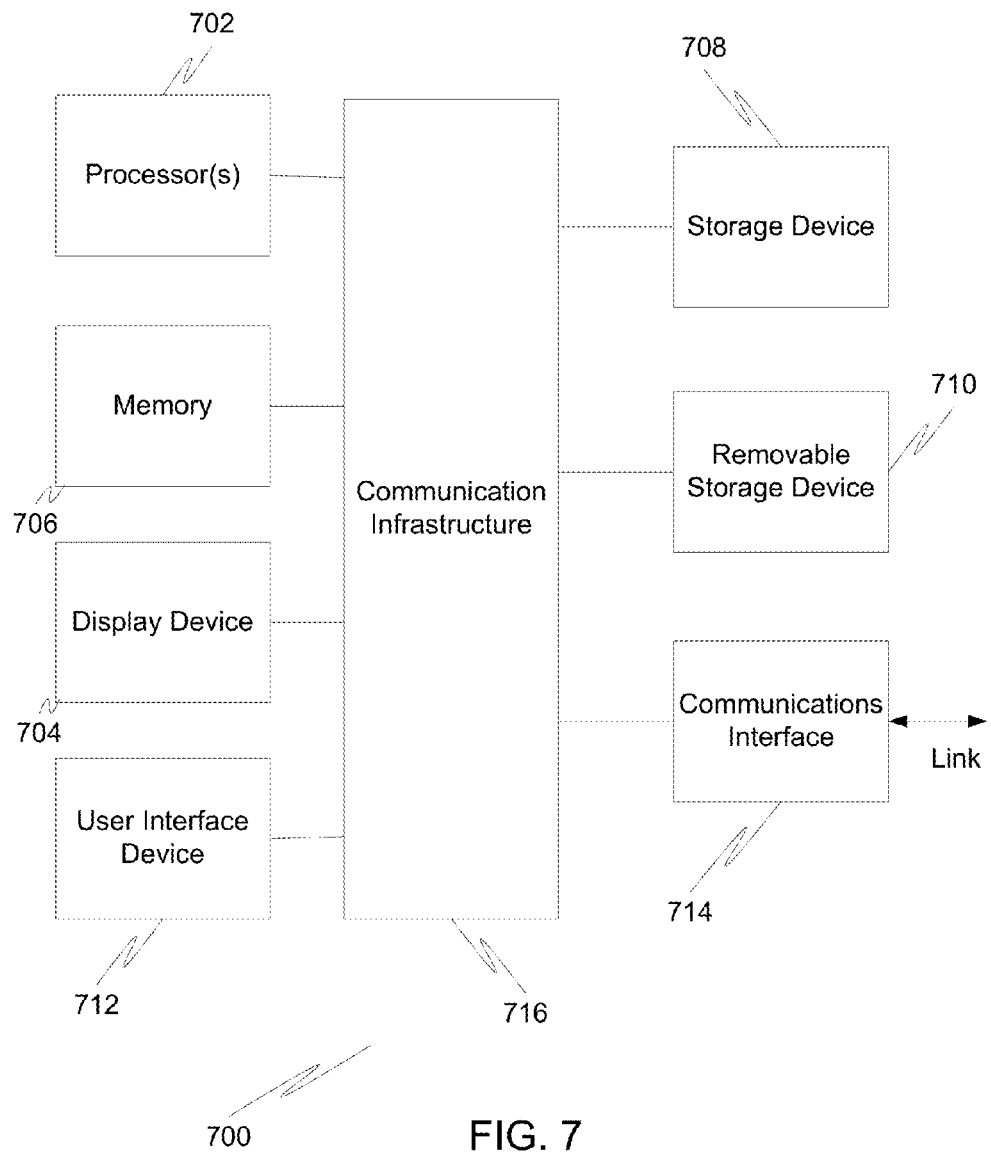
FIG. 7 is a high level block diagram showing a computer system used in embodiments of the present invention.

FIG. 7 is a high level block diagram showing a computer system 700, which is suitable for implementing the controller 612 used in embodiments of the present invention. The computer system may have many physical forms ranging from an integrated circuit, a printed circuit board, and a small handheld device up to a super computer. The computer system 700 includes one or more processors 702, and further can include an electronic display device 704 (for displaying graphics, text, and other data), a main memory 706 (e.g., random access memory (RAM)), storage device 708 (e.g., hard disk drive), removable storage device 710 (e.g., optical disk drive), user interface devices 712 (e.g., keyboards, touch screens, keypads, mice or other pointing devices, etc.), and a communication interface 714 (e.g., wireless network interface). The communication interface 714 allows software and data to be transferred between the computer system 700 and external devices via a link. The system may also include a communications infrastructure 716 (e.g., a communications bus, cross-over bar, or network) to which the aforementioned devices/modules are connected.

Information transferred via communications interface 714 may be in the form of signals such as electronic, electromagnetic, optical, or other signals capable of being received by communications interface 714, via a communication link that carries signals and may be implemented using wire or cable, fiber optics, a phone line, a cellular phone link, a radio frequency link, and/or other communication channels. With such a communications interface, it is contemplated that the one or more processors 702 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Figure 8:
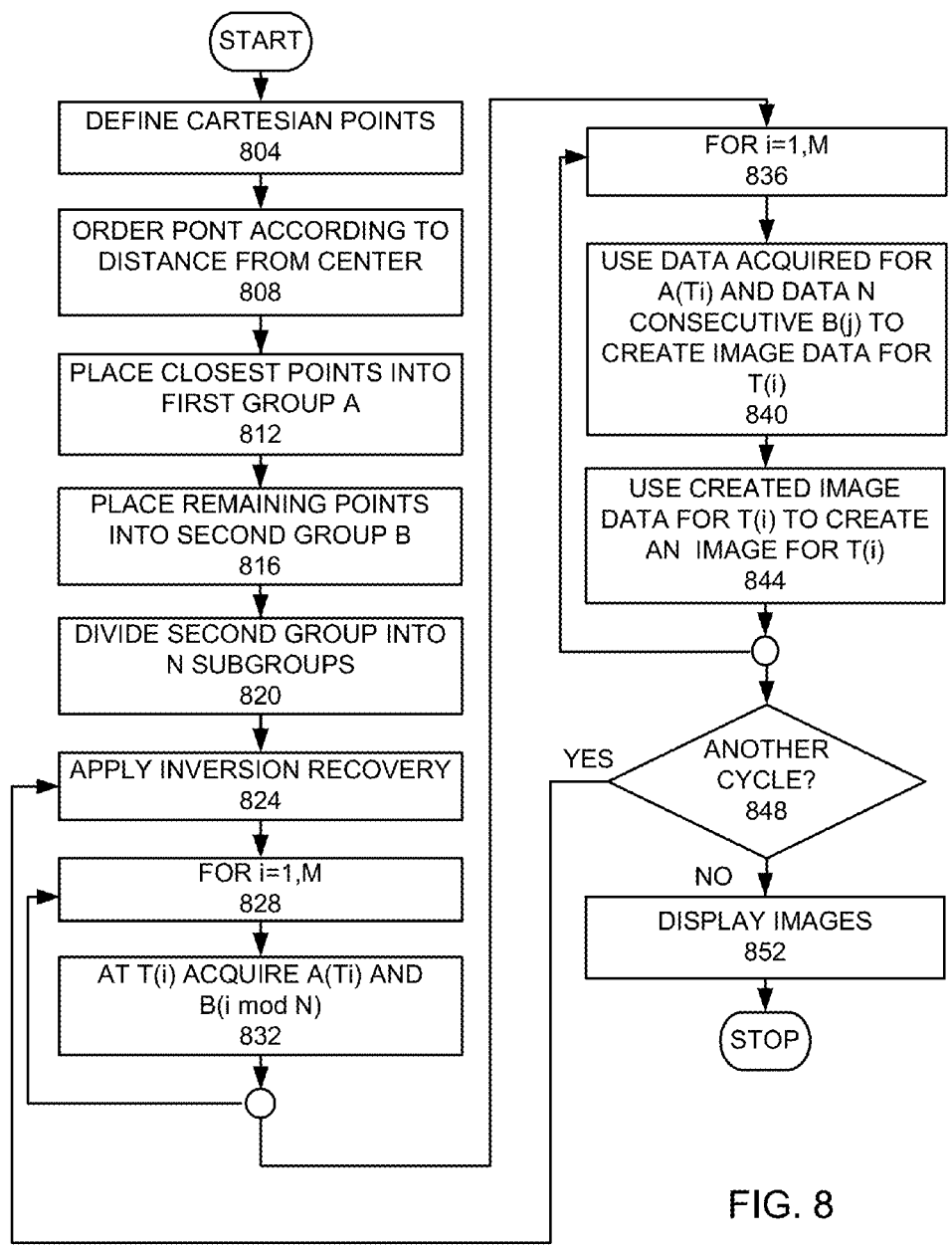
FIG. 8 is a flow chart of a process used in an embodiment of the invention.

FIG. 8 is a flow chart of a process used in an embodiment of the invention. A plurality of Cartesian points are defined on a $k_y$-$k_z$ plane with a center, wherein each of the plurality of Cartesian points has a $k_r$, wherein $k_r$ is a distance from a Cartesian point of the plurality of Cartesian points to the center (step 804). Each of the plurality of Cartesian points is ordered according to $k_r$, the distance from a point to the center (step 808). The Cartesian points are divided placing the Cartesian points closest to the center into a first group, Group A, (step 812) and the remaining Cartesian points into a second group, Group B (step 816). This causes the Cartesian points in the first group to be within a radius R from the center and the Cartesian points in the second group to be outside of the radius R from the center. The second group is divided into N subgroups, where N is a whole number greater than or equal to two (step 820). In one example, N=3, so that there are 3 subgroups. Preferably, the subgroups have an incoherent point spread function. In the specification and claims, the subgroups have an incoherent point spread function when the weighted Fourier transform of the Cartesian points in k-space into the frequency domain results in an incoherent point spread function with minimal or no artifacts.

An inversion recovery (IR) radio frequency is applied by the MRI system 600 to a subject, so that a net longitudinal magnetization in the subject is substantially inverted and begins to relax back to equilibrium (step 824).

M acquisitions are made in a loop at different times $T_1$ through $T_M$ to obtain M phases of acquired data (step 828). For each acquisition time $T_i$ acquisitions for all Cartesian points in the first group and the subgroup $B_{i\ mod\ N}$ are made (step 832). This causes the acquisition by the subgroups to be sequential and cyclical. In this embodiment a loop is provided for i going from 1 to M. In an example, M=6, so that 6 time phases are collected. Therefore, for time phase 1, A(T1) (A at time 1) and the first subgroup (B(1)) are acquired. At the second phase, A(T2) and B(2) are acquired. At the third phase, A(T3) and B(3) are acquired. At the fourth phase A(T4) and B(1), since 1=4 mod 3, is acquired. Therefore, the acquisition for different subgroups occurs in a sequence, and the sequence is repeated in a cycle, causing the acquisition by the subgroups to be sequential and cyclical for the M different time periods.

Images are generated from the acquired data. In this example a loop is used with i going from 1 to M (step 836). Image data for time $T_i$ is generated using only acquired data for $A(T_i)$ and acquired data for at least N consecutive subgroups of B (step 840). For example, to generate image data for time 1 (T1), data from A(T1) and B1 acquired at T1, B2 acquired at T2, and B3, acquired at T3 would be used. B1, B2, and B3 acquired are T1, T2, and T3 would be N=3 consecutive subgroups of B. To generate image data for time 4 (T4), data from A(T4), B(3) acquired at T3, B(1) acquired at T4, and B(2) acquired at T5 would be used. In this example, B(3) acquired at T3, B(1) acquired at T4, and B(2) acquired at T5 would be 3 consecutive subgroups acquired within a cycle. One of the N consecutive subgroups is the acquisition of a subgroup that occurred during the time Ti. The remaining acquired subgroups in the at least N consecutive subgroups are adjacent to another acquired subgroup in the at least N consecutive subgroups. M is ideally an integral multiple of N. The image data for $T_i$ is used to create an image for $T_i$ (step 844). If another cycle is desired (step 848) the process returns to the application of the IR radio frequency (step 824). Otherwise the images are displayed (step 852).

In other embodiments some of the images may be displayed before all of the cycles are completed.

Other embodiments may generate at least two images, but less than all N images. For example, an embodiment may use acquired k-space data for the first group of Cartesian points at a first time period of the N different time periods and k-space data from all of the subgroups of Cartesian points within a cycle to create first image data of the subject for the first time period and use acquired k-space data for the first group of Cartesian points at a second time period of the N different time periods and k-space data from all of the subgroups of Cartesian points within a cycle to create image data of the subject for the second time period. This embodiment would use the first image data to create a first image and the second image data to create a second image. The first and second images would be displayed. In another embodiment, the first image data and the second image data would be combined to create a relaxation map.

Preferably N is between 3 and 6 inclusive. Preferably, M is an integral multiple of N.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A method for providing an image of a subject in a magnetic resonance imaging MRI system, comprising:
   defining a plurality of Cartesian points on a $k_y$-$k_z$ plane with a center, wherein each of the plurality of Cartesian points has a $k_r$, wherein $k_r$ is a distance from a Cartesian point of the plurality of Cartesian points to the center;
   dividing the plurality of Cartesian points into a first group (Group A) and a second group (Group B), wherein all of the Cartesian points in the first group have a $k_r$ that is less than or equal to $k_r$ of all of the Cartesian points in the second group;
   dividing the second group into N subgroups, wherein N is a whole number greater than or equal to two, wherein the subgroups have an incoherent point spread function;
   applying an inversion recovery (IR) radio frequency to the subject such that a net longitudinal magnetization in the subject is substantially inverted and begins to relax back to equilibrium;
   acquiring k-space data for the first group of Cartesian points for M different time periods, wherein k-space data is acquired for only one sub-group for each time period of the M different time periods, and wherein k-space data is acquired for each subgroup sequentially and cyclically for the M different time periods;

for each time period i of the M different time periods, using acquired k-space data for the first group of Cartesian points at time period i and k-space data from N consecutive subgroups of Cartesian points where one of the N consecutive subgroups is the subgroup that is acquired during time period i to create image data of the subject for first time period i.

2. The method, as recited in claim 1, further comprising:

for each time period i for the M different time periods, using the image data for time period i to create an image for time period i; and displaying the image for time period.

3. The method, as recited in claim 1, wherein the image data from a plurality of time periods are combined to create a relaxation map.

4. The method, as recited in claim 1, wherein the first plurality of Cartesian points are within a radial sector of the circle, and wherein the Cartesian points within the first group are all Cartesian points in the radial sector at or within a radius of R from the center of the circle and wherein the Cartesian points within the second group are all Cartesian points in the radial sector at or beyond the radius of R from the center of the circle.

5. The method, as recited in claim 1, wherein the Cartesian points within the first group are Cartesian points in the circle at or within a radius of r from the center of the circle and wherein the Cartesian points within the second group are Cartesian points in the circle at or beyond the radius of r from the center of the circle.

6. The method, as recited in claim 1, wherein Cartesian points in each subgroup are dispersed as much as possible.

7. The method, as recited in claim 1, wherein the Cartesian points in each subgroup are chosen by at least one of dithered spiral interleaving, random selection, or pseudo-random selection.

8. The method, as recited in claim 1, further comprising:

for each time period i for the M different time periods, using the image data for time period i to create an image for time period i, which provides a plurality of images;

displaying the plurality of images; and using the plurality of images to provide multicontrast images.

9. The method, as recited in claim 8, wherein the Cartesian points in each subgroup are chosen by at least one of dithered spiral interleaving, random selection, or pseudo-random selection.

10. The method, as recited in claim 9, wherein N is between 3 and 6 inclusive.

11. The method, as recited in claim 10, wherein M is a multiple of N.

12. The method, as recited in claim 11, wherein Cartesian points in each subgroup are dispersed as much as possible.

13. The method, as recited in claim 12, wherein the multicontrast images are multicontrast images of a brain.

14. The method, as recited in claim 12, wherein the first plurality of Cartesian points are within a radial sector of the circle, and wherein the Cartesian points within the first group are all Cartesian points in the radial sector at or within a radius of R from the center of the circle and wherein the Cartesian points within the second group are all Cartesian points in the radial sector at or beyond the radius of R from the center of the circle.

15. The method, as recited in claim 12, wherein the Cartesian points within the first group are Cartesian points in the circle at or within a radius of r from the center of the circle and wherein the Cartesian points within the second group are Cartesian points in the circle at or beyond the radius of r from the center of the circle.

16. The method, as recited in claim 1, wherein N is between 3 and 6 inclusive.

17. The method, as recited in claim 1, wherein M is a multiple of N.

18. The method, as recited in claim 1, wherein the N subgroups are interleaved.

* * * * *